United States Patent [19]

Niznick et al.

[11] Patent Number: 5,427,527
[45] Date of Patent: Jun. 27, 1995

[54] DENTAL IMPLANT METHOD OF INSTALLATION

[75] Inventors: Gerald A. Niznick, Las Vegas, Nev.; Anthony Rinaldi, Philadelphia, Pa.; Leonard I. Linkow, Fort Lee, N.J.

[73] Assignee: Vent Plant Corporation, Philadelphia, Pa.

[21] Appl. No.: 66,561

[22] Filed: May 25, 1993

[51] Int. Cl.⁶ .................................................. A61C 8/00
[52] U.S. Cl. ........................................................ 433/174
[58] Field of Search .................................... 433/173, 174

[56] References Cited

U.S. PATENT DOCUMENTS

| | | | |
|---|---|---|---|
| 2,609,604 | 9/1952 | Sprague | 433/174 |
| 3,762,058 | 6/1972 | Nikoghossian | 433/174 |
| 4,406,623 | 9/1983 | Grafelmann et al. | 433/174 |
| 4,547,157 | 10/1985 | Driskell | 433/173 |
| 4,932,868 | 6/1990 | Linkow et al. | 433/174 |
| 5,000,686 | 3/1991 | Lazzara et al. | 433/174 |
| 5,074,790 | 12/1991 | Bauer | 433/174 |

FOREIGN PATENT DOCUMENTS

2667499  4/1992  France ........................ 433/173

OTHER PUBLICATIONS

English translation of French Patent Application No. 2 667 499 (10 pages) with an Affidavit of Accuracy by Mikael E. Poulsen dated Nov. 5, 1993 (1 page).
Dentsply/Implant Division, "The Friction-Fit Hex-Lock Abutment", 1992, 1 page (double-sided).

*Primary Examiner*—John J. Wilson
*Attorney, Agent, or Firm*—Darby & Darby

[57] ABSTRACT

A dental implant system utilizes a threaded implant which is cylindrical in form and has a large number of longitudinal channels so it can be (i) screwed into place in a bore hole in the patient's bone, (ii) pushed into place or (iii) first pushed into place and then turned to anchor it in bone ridges formed when it is pushed into place. Also an implant is given a conical shape it can be used for supporting artificial teeth in a residual ridge crest of a patient by drilling a smaller than normal cylindrical hole in the crest and carefully inserting the conical implant so that the bone is spread and makes additional contact with the implant.

3 Claims, 3 Drawing Sheets

FIG. 3B
FIG. 3A
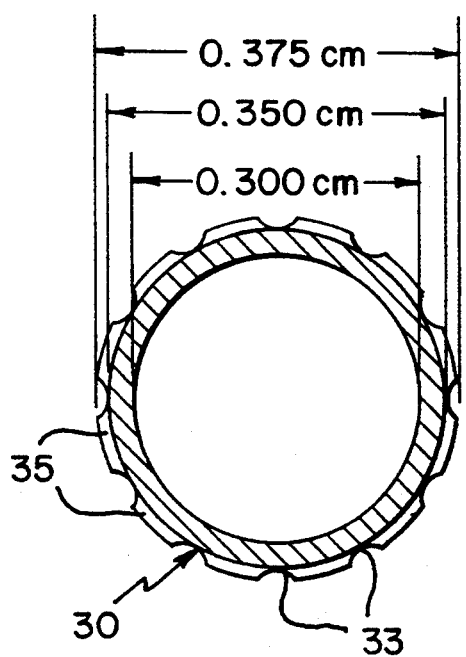
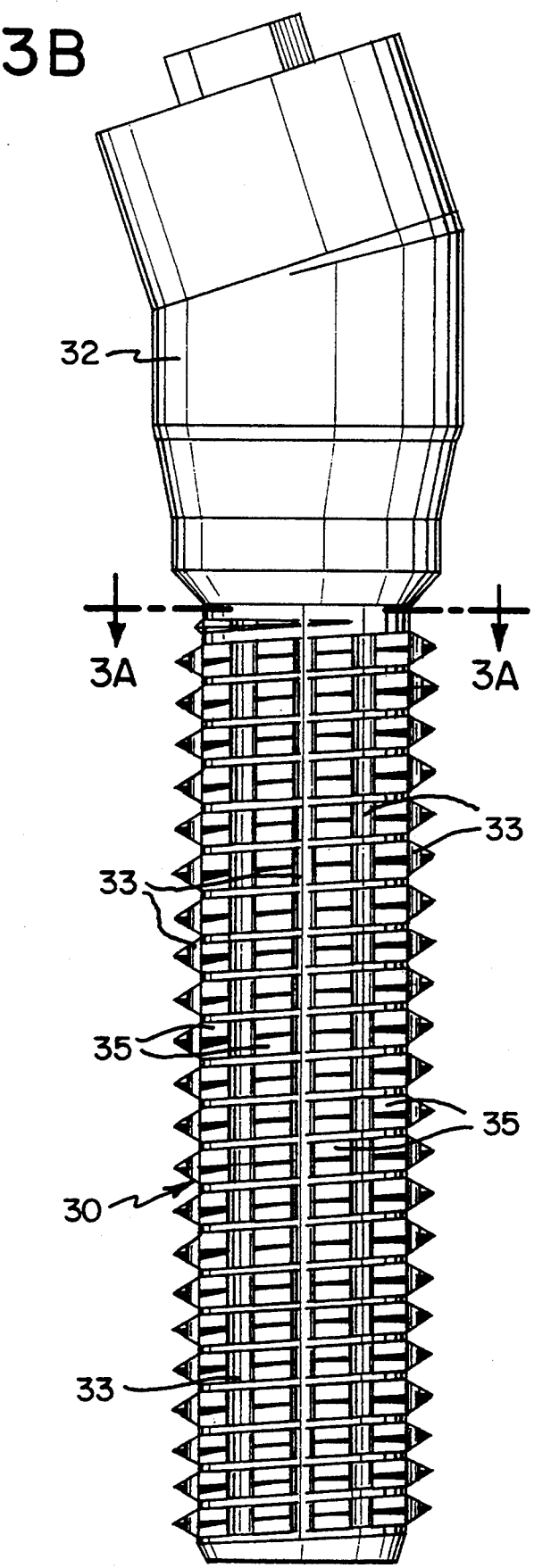

DENTAL IMPLANT METHOD OF INSTALLATION

TECHNICAL FIELD

This invention relates to dental implant devices and, more particularly, to screw-type dental implant systems.

BACKGROUND ART

Screw-type implants are now well-known. U.S. Pat. No. 3,499,222 of L. I. Linkow et al. discloses screw-type implants which may be buried in the alveolar ridge crest bone of a patient in an edentulous region. The implant has a threaded lower portion which may be screwed into an opening created in the bone after the tissue has been displaced. A coronal portion protrudes above the bone and is used to support an artificial dental appliance, e.g., an artificial tooth or bridge.

In more recent years, submergible implants have been created in which the threaded portions of the implants can be completely embedded in the bone. They may then be covered with tissue and allowed to remain in place while new bone grows around the implant and through vent holes within the implant. Once it is firmly anchored in new bone, the tissue is reopened and an abutment or upper post portion is screwed into the implant portion and is used to mount the artificial dental device. Submergible implants of this type are disclosed in U.S. Pat. No. 4,713,004 of Linkow et al.

It is advantageous, when installing an implant portion in the patient's jawbone, for the implant to self-tap into the bore hole created in the patient's jawbone because this causes the implant to be better anchored in the bone. As shown in U.S. Pat. No. 4,713,004 of Linkow et al, such an implant may include a cylindrical body with an exterior threaded region that contains a longitudinal channel through a portion of the outer parts of the threads. The channel is wider toward its bottom. One side of the channel is at a right angle to the implant circumference so as to create a cutting edge that creates a self-tapping capability for the implant when it is threaded into a bore or opening in the patient's bone. The channel guides bone chips, created during the threading of the implant, toward the base of the bore in the bone. The bone chips created during the self-tapping operation promote faster bone growth due to their autogenous nature.

The majority of submergible dental implants sold today have an external hexagonal head ("hex-head") which projects from the outer end and is used to couple the implant to an insertion device, e.g. a wrench. This projecting hex-head is also used in attaching the implant to an abutment or post having a matching hex-shaped cavity that receives the projection. Such projecting heads and cavities may be referred to as "coupling surfaces."

Certain areas of the jawbone, such as the thin ("bucco-lingual") residual ridges located primarily in the maxilla, are too thin to allow drilling with a cylindrical drill of The preferred size range in order to create the bore hole. This, in turn, leads to the use of narrower implants. However, due to the decreased surface area of bone contact and their small diameter, these narrower implants are much more likely to fail.

DISCLOSURE OF THE INVENTION

This invention relates to improvements in the implant portion of screw-type dental implants that are achieved by means of various designs of the implant portion that permit stable engagement with surrounding bone (e.g. a conical shape or a cylindrical shape with bone engaging threads or projections).

In an illustrative embodiment of the invention, the implant portion has relatively narrow threads and a plurality of channels spaced about the circumference of a cylindrical implant portion. As a result, the implant portion may be pushed into place in a bore hole created in the patient's alveolar ridge, instead of being screwed into place. Since the threads are narrow, and the bone is relatively soft, channels are gouged in the bone at the location of the threads, while ridges of bone are formed at the location of the channels. When installed, the bone ridges prevent accidental rotation of the implant. However, if desired, once the implant portion is fully inserted in the hole, it may be given a slight rotation, e.g. by means of a wrench applied to its projecting hex-head, so that the portions of thread between the longitudinal channels can cut into the ridges of bone to anchor the implant portion in place.

The present invention also contemplates conical implant portions inserted into cylindrical bore holes in narrow alveolar ridges. When inserted, the upper portion of the implant (which is somewhat too large for the bore hole) spreads the adjacent bone of the ridge, thus enlarging the amount of bone which can be used to anchor the implant. The upper part of the implant where most of the stress is concentrated is also larger. The increase in bone and implant contact surface area, and the size of the upper part of the implant due to the use of a conical shape, can be critical to the long-term stability of an implant inserted into a thin residual alveolar ridge.

BRIEF DESCRIPTION OF THE DRAWINGS

The foregoing and other features of the present invention will be more readily apparent from the following detailed description and drawings of illustrative embodiments of the invention, in which:

FIG. 3A shows a cross sectional view of a multi-channel threaded implant portion shown in FIG. 3B taken along the line 3A—3A; and FIG. 3B shows a side view of the implant portion of FIG. 3A.

DESCRIPTION OF THE ILLUSTRATIVE EMBODIMENTS

Figure 1A:
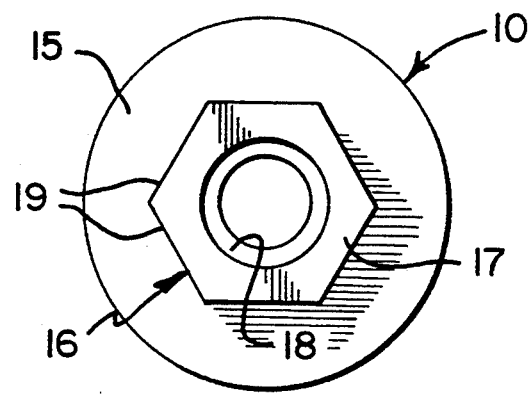
FIG. 1A is a top view of a typical prior art hex-head implant showing the surface which would couple to an abutment.
Figure 1B:
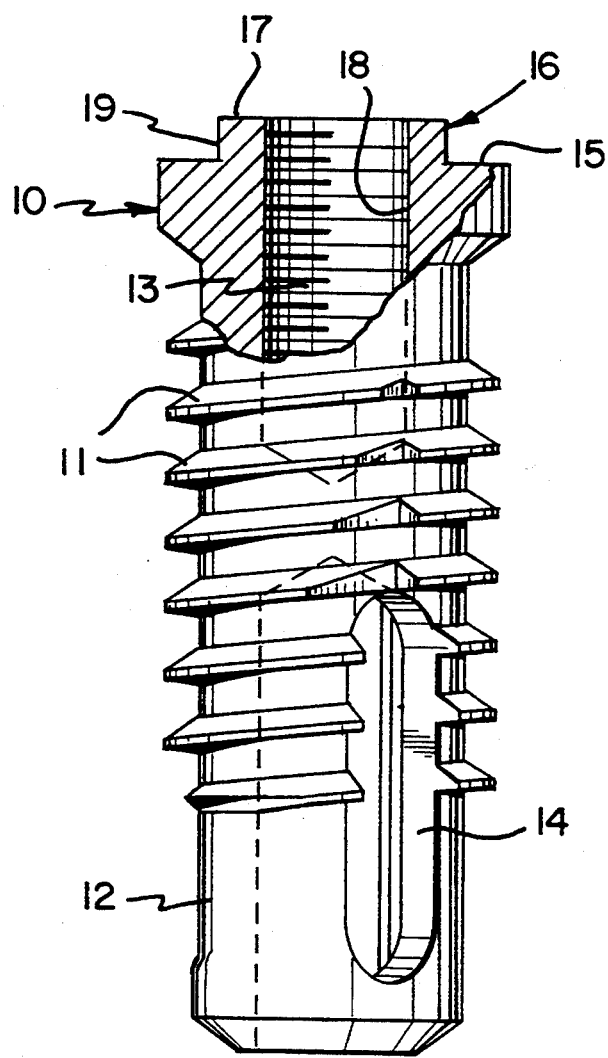
FIG. 1B is a side view of a prior art implant, with the hashed-line portions of the drawing representing a cross-sectional cut-away.

FIGS. 1A and 1B illustrate a typical prior art implant portion 10, with the hashed-line portions of the drawing representing a cross-sectional cut-away. The implant body 12 is generally cylindrical and its exterior sides will normally have threads 11, which may be self-tapping to facilitate anchoring the implant in the bone. A vent hole 14 passes through body 12. After the implant has been installed, bone may grow through the vent, thus further anchoring the implant.

FIG. 1A shows a top view of a typical external hexagonal projecting head 16 ("hex-head") which provides the coupling surfaces of an implant portion that engage the coupling surfaces of an abutment. The hex-head coupling surfaces include a lower surface 15 which forms the base of the hex-head, an upper surface 17 which forms the cap of the hex-head and a threaded aperture 18 which extends through the hex-head and into the implant portion. In the side view of FIG. 1B the side walls 19 of the hex-head are shown along with the threads 13 of the aperture 18 for the abutment screw.

Thin (bucco-lingual) residual ridges located in, but not limited to, the maxilla, limit the width of cylindrical drills and implants that can be used. Therefore narrow implants of insufficient surface area have to be used, but these have a greater tendency to fail.

Figure 2:
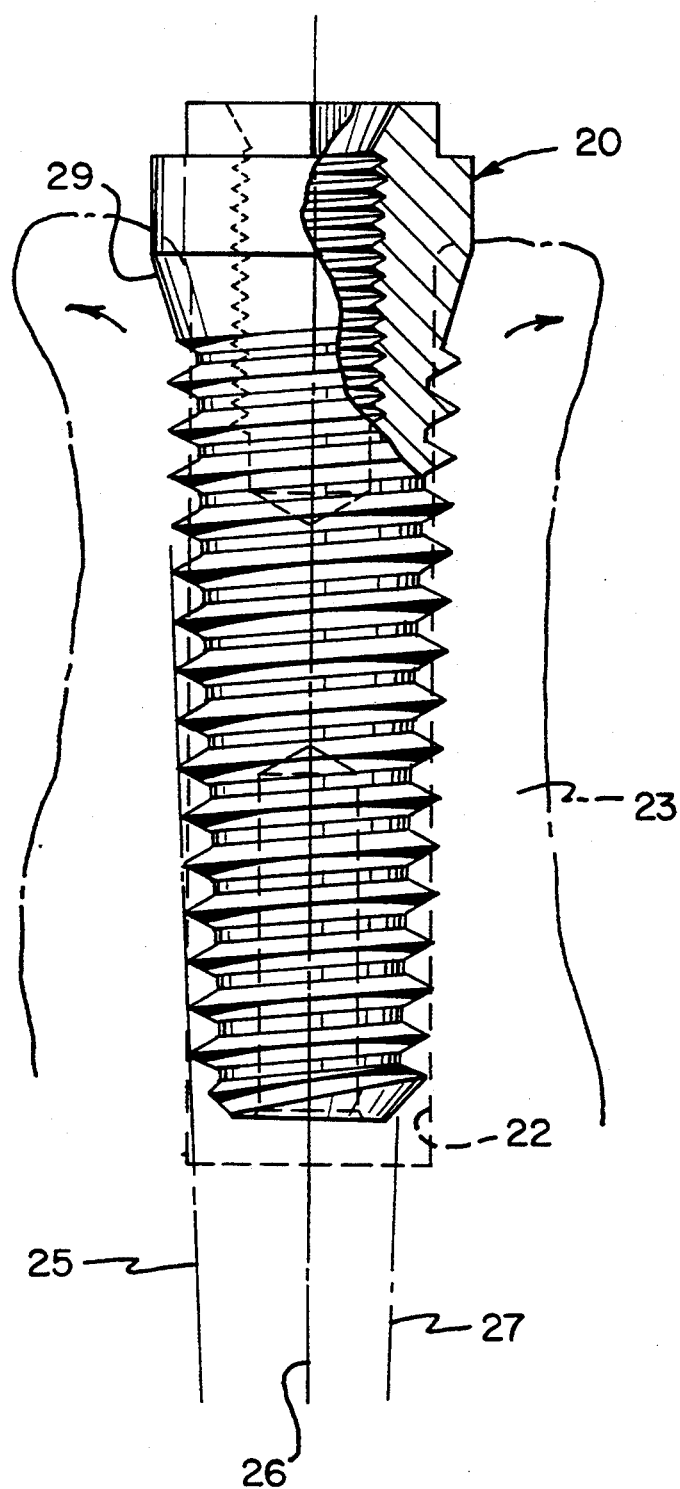
FIG. 2 shows a side view of a conical implant inserted in a residual alveolar ridge crest.

As shown in FIG. 2, a conical implant 20 may be screwed into a smaller cylindrical hole 22 (shown in dotted line) in a residual ridge bone 23. Due to the conical nature of the implant, the implant spreads the thin residual ridge as represented by the arrows in FIG. 2 and successfully engages a larger surface area implant. The spread bone should preferably be allowed to heal before the implant is put into active use by mounting an abutment on it. Conical implants were developed to be inserted into conical voids in bone of about the same size which are created by the extraction of natural teeth which have become diseased. Thus, the present invention represents a new use of such implants.

The conical implant of the present invention can be with or without a cutter channel mechanism, and with or without an external hex mechanism for attachment to an abutment. The angle of taper for the conical implant of FIG. 2 is illustrated by the angle between reference lines 25 and 26 or between reference lines 26 and 27, which is about 2°.

With a 2° taper over a threaded portion of about 7.5 mm in length, as shown in FIG. 2, the diameter of the bore hole is about 3.3 mm, the diameter of the implant at the top of the threads is about 3.6 mm and the diameter at the base surface of the contact area 29 of the implant it is about 4 mm. This shows that the implant is significantly stronger at its top portion than if it were the diameter of the bore hole over its entire length. The angle of taper for the conical implants of the invention is preferably between about 1° and about 10°, more preferably between about 1° and 3° (with the angle measured between the main axis of the implant 26 and the tapered surfaces 25, 27). The entire length of the implant need not be conical as shown in FIG. 2. Some portions may be cylindrical, so long as about 50% of the length is conical. In all cases, the upper portion of the implant (having the coupling surface 29) will have the greater diameter.

The conical implants according to the invention may have any maximum diameter suitable for implants. However, it is anticipated that these implants will most often be used in the residual ridges. For this purpose, a maximum diameter of between about 3 mm and about 4 mm is preferred, with an overall length of about 10 mm.

FIGS. 3A and 3B illustrate cross-sectional and side views of a cylindrical threaded implant 30 with an angled abutment 32. The threads of this implant are interrupted by a plurality of longitudinal channels 33. As can be seen from the cross sectional view of FIG. 3A, the channels are so numerous (i.e. 12 in FIG. 3A) and closely spaced as to give a serrated appearance. In a typical embodiment the implant has an outer diameter for its threads of 0.375 cm. The diameter at the depth of the channels is 0.350 cm, while the inner diameter of the threads is 0.300 cm. Thus the channels in this illustrative embodiment are 12.5 mm deep. However, channels as deep as 25 mm are acceptable.

In one use for the implant of FIG. 3, it is screwed into a bore hole in the jaw of a patient in a conventional manner. With this use the bore hole is made to have dimensions that approximate those of the inner diameter of the screw threads. In a second use, the implant is merely pushed into place in the bore hole. In this use, the bore hole has a diameter about equal to the diameter at the depth of the channels. During this procedure the sections 35 of the threads between the channels 33, crush the surrounding bone to a slight extent as the implant is pushed into the hole. As a result, raised ridges of bone are created in the areas of the channels. These ridges prevent rotation of the implant. As another use, the implant is pushed into place and then, using a wrench over an external or internal hex, it is rotated slightly so the thread sections cut into the adjacent bone ridges to lock the implant in place more securely. As a result, the same implant can be used for three different insertion techniques. All that needs to be done to use these techniques is to adjust the size of the bore hole.

While the invention has been particularly shown and described with reference to preferred embodiments thereof, it will be understood by those skilled in the art that various changes in form and details may be made therein without departing from the spirit and scope of the invention.

What is claimed is:

1. A method of mounting an implant in a thin residual alveolar ridge crest, comprising:
    forming a cylindrical bore hole in the ridge crest that is of a size that it is well within the available bone;
    introducing a conical threaded implant in to the bore hole in the patient's ridge crest, a lower part of the implant being smaller in diameter than the bore hole and an upper part of the implant being greater in diameter than the bore hole;
    installing said implant into said bore hole such that said installation causes the upper part of the implant to spread the bone about the bore hole, and
    after the implant is fully installed, allowing a period of time to pass sufficient for the spread bone to heal.

2. The method of claim 1, wherein the taper of said conical implant ranges from about 1° to about 10°.

3. The method of claim 2, wherein the taper is about 2°.

* * * * *